United States Patent
Imran et al.

(10) Patent No.: US 9,919,149 B2
(45) Date of Patent: Mar. 20, 2018

(54) IMPLANTABLE FLEXIBLE CIRCUIT LEADS AND METHODS OF USE

(71) Applicant: St. Jude Medical Luxembourg Holdings SMI S.A.R.L. ("SJM LUX SML"), Luxembourg (LU)

(72) Inventors: Mir A. Imran, Los Altos, CA (US); Albert G. Burdulis, San Francisco, CA (US); Matthew G. Hills, Los Altos, CA (US); Eyad Kishawi, San Mateo, CA (US)

(73) Assignee: St. Jude Medical Luxembourg Holdings SMI S.A.R.L. ("SJM LUX SMI"), Luxembourg (LU)

( * ) Notice: Subject to any disclaimer, the term of this patent is extended or adjusted under 35 U.S.C. 154(b) by 0 days.

(21) Appl. No.: 15/635,006

(22) Filed: Jun. 27, 2017

(65) Prior Publication Data

US 2017/0291026 A1 Oct. 12, 2017

Related U.S. Application Data

(63) Continuation of application No. 15/131,848, filed on Apr. 18, 2016, now abandoned, which is a continuation of application No. 11/952,062, filed on Dec. 6, 2007, now Pat. No. 9,314,618.

(60) Provisional application No. 60/873,459, filed on Dec. 6, 2006, provisional application No. 60/873,496, filed on Dec. 6, 2006.

(51) Int. Cl.
A61B 5/04 (2006.01)
A61N 1/00 (2006.01)
A61N 1/05 (2006.01)
H05K 1/11 (2006.01)

(52) U.S. Cl.
CPC ......... *A61N 1/0553* (2013.01); *A61N 1/0556* (2013.01); *H05K 1/118* (2013.01)

(58) Field of Classification Search
CPC ..... A61N 1/0553; A61N 1/0556; H05K 1/118
See application file for complete search history.

(56) References Cited

U.S. PATENT DOCUMENTS

| | | | | |
|---|---|---|---|---|
| 4,573,481 A | * | 3/1986 | Bullara | A61N 1/0556 607/118 |
| 4,976,711 A | * | 12/1990 | Parins | A61B 18/1492 606/48 |
| 5,344,438 A | * | 9/1994 | Testerman | A61N 1/0556 600/373 |
| 5,720,099 A | * | 2/1998 | Parker | A61N 1/05 216/13 |
| 6,413,255 B1 | * | 7/2002 | Stern | A61B 18/14 606/41 |

(Continued)

*Primary Examiner* — Lindsey G Wehrheim

(57) ABSTRACT

Devices, systems and methods are provided for stimulation of tissues and structures within a body of a patient. In particular, implantable leads are provided which are comprised of a flexible circuit. Typically, the flexible circuit includes an array of conductors bonded to a thin dielectric film. Example dielectric films include polyimide, polyvinylidene fluoride (PVDF) or other biocompatible materials to name a few. Such leads are particularly suitable for stimulation of the spinal anatomy, more particularly suitable for stimulation of specific nerve anatomies, such as the dorsal root (optionally including the dorsal root ganglion).

20 Claims, 17 Drawing Sheets

(56) References Cited

U.S. PATENT DOCUMENTS

| | | | |
|---|---|---|---|
| 6,849,075 B2* | 2/2005 | Bertolero | A61B 1/12 |
| | | | 128/898 |
| 6,973,342 B1* | 12/2005 | Swanson | A61B 5/04 |
| | | | 600/378 |
| 2004/0147992 A1* | 7/2004 | Bluger | A61N 1/0541 |
| | | | 607/116 |
| 2006/0052845 A1* | 3/2006 | Zanella | A61N 1/326 |
| | | | 607/68 |
| 2006/0155344 A1* | 7/2006 | Rezai | A61N 1/0551 |
| | | | 607/46 |
| 2006/0195169 A1* | 8/2006 | Gross | A61N 1/0546 |
| | | | 607/116 |
| 2006/0200121 A1* | 9/2006 | Mowery | A61B 18/1477 |
| | | | 606/41 |
| 2008/0119711 A1* | 5/2008 | Nikumb | A61N 1/0531 |
| | | | 600/378 |

\* cited by examiner

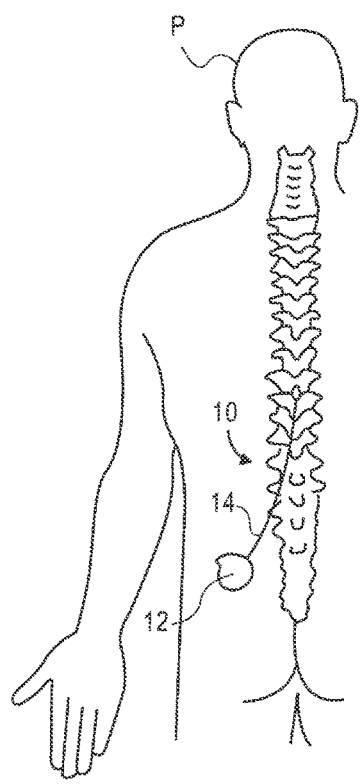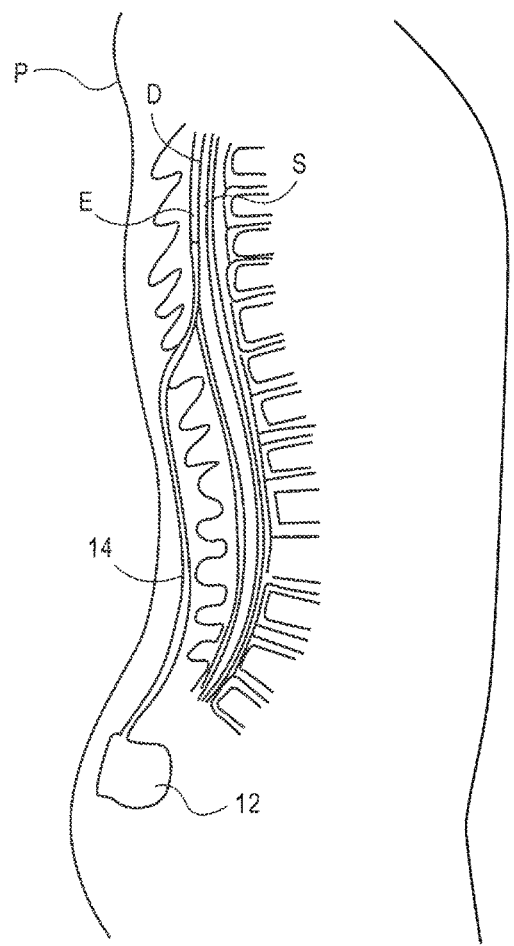
FIG. 1A
(PRIOR ART)
FIG. 1B
(PRIOR ART)

IMPLANTABLE FLEXIBLE CIRCUIT LEADS AND METHODS OF USE

CROSS-REFERENCES TO RELATED APPLICATIONS

This application is a continuation of U.S. patent application Ser. No. 15/131,848, filed Apr. 18, 2016, which is a continuation of U.S. patent application Ser. No. 11/952,062, filed Dec. 6, 2007 (now U.S. Pat. No. 9,314,618), which claims priority of U.S. Provisional Patent Application No. 60/873,459, filed Dec. 6, 2006; and U.S. Provisional Patent Application No. 60/873,496, filed Dec. 6, 2006, all of which are incorporated herein by reference for all purposes.

BACKGROUND

The application of specific electrical energy to the spinal cord for the purpose of managing pain has been actively practiced since the 1960s. It is known that application of an electrical field to spinal nervous tissue can effectively mask certain types of pain transmitted from regions of the body associated with the stimulated nervous tissue. Such masking is known as paresthesia, a subjective sensation of numbness or tingling in the afflicted bodily regions. Application of electrical energy has been based on the gate control theory of pain. Published in 1965 by Melzack and Wall, this theory states that reception of large nerve fiber information, such as touch, sense of cold, or vibration, would turn off or close the gate to reception of painful small nerve fiber information. The expected end result would, therefore, be pain relief. Based on the gate control theory, electrical stimulation of large fibers of the spinal cord cause small fiber information to be reduced or eliminated at that spinal segment and all other information downstream from that segment would be reduced or eliminated as well. Such electrical stimulation of the spinal cord, once known as dorsal column stimulation, is now referred to as spinal cord stimulation or SCS.

FIGS. 1A-1B illustrate conventional placement of an SCS system 10. Conventional SCS systems include an implantable power source or implantable pulse generator (IPG) 12 and an implantable lead 14. Such IPGs 12 are similar in size and weight to pacemakers and are typically implanted in the buttocks of a patient P. Using fluoroscopy, the lead 14 is implanted into the epidural space E of the spinal column and positioned against the dura layer D of the spinal cord S, as illustrated in FIG. 1B. The lead 14 is implanted either through the skin via an epidural needle (for percutaneous leads) or directly and surgically through a mini laminotomy operation (for paddle leads).

FIG. 2 illustrates example conventional paddle leads 16 and percutaneous leads 18. Paddle leads 16 typically have the form of a slab of silicon rubber having one or more electrodes 20 on its surface. Example dimensions of a paddle lead 16 is illustrated in FIG. 3. Percutaneous leads 18 typically have the form of a tube or rod having one or more electrodes 20 extending therearound. Example dimensions of a percutaneous lead 18 is illustrated in FIG. 4.

Implantation of a percutaneous lead 18 typically involves an incision over the low back area (for control of back and leg pain) or over the upper back and neck area (for pain in the arms). An epidural needle is placed through the incision into the epidural space and the lead is advanced and steered over the spinal cord until it reaches the area of the spinal cord that, when electrically stimulated, produces a comfortable tingling sensation (paresthesia) that covers the patient's painful area. To locate this area, the lead is moved and turned on and off while the patient provides feedback about stimulation coverage. Because the patient participates in this operation and directs the operator to the correct area of the spinal cord, the procedure is performed with local anesthesia.

Implantation of paddle leads 16 typically involves performing a mini laminotomy to implant the lead. An incision is made either slightly below or above the spinal cord segment to be stimulated. The epidural space is entered directly through the hole in the bone and a paddle lead 16 is placed over the area to stimulate the spinal cord. The target area for stimulation usually has been located before this procedure during a spinal cord stimulation trial with percutaneous leads 18.

Although such SCS systems have effectively relieved pain in some patients, these systems have a number of drawbacks. To begin, as illustrated in FIG. 5, the lead 14 is positioned upon the spinal cord dura layer D so that the electrodes 20 stimulate a wide portion of the spinal cord and associated spinal nervous tissue. The spinal cord is a continuous body and three spinal levels of the spinal cord are illustrated. For purposes of illustration, spinal levels are sub-sections of the spinal cord S depicting that portion where the dorsal root DR and ventral root VR join the spinal cord S. The peripheral nerve N divides into the dorsal root DR and the dorsal root ganglion DRG and the ventral nerve root VR each of which feed into the spinal cord S. An ascending pathway 17 is illustrated between level 2 and level 1 and a descending pathway 19 is illustrated from level 2 to level 3. Spinal levels can correspond to the vertebral levels of the spine commonly used to describe the vertebral bodies of the spine. For simplicity, each level illustrates the nerves of only one side and a normal anatomical configuration would have similar nerves illustrated in the side of the spinal cord directly adjacent the lead.

Motor spinal nervous tissue, or nervous tissue from ventral nerve roots, transmits muscle/motor control signals. Sensory spinal nervous tissue, or nervous tissue from dorsal nerve roots, transmits pain signals. Corresponding dorsal and ventral nerve roots depart the spinal cord "separately"; however, immediately thereafter, the nervous tissue of the dorsal and ventral nerve roots are mixed, or intertwined. Accordingly, electrical stimulation by the lead 14 often causes undesirable stimulation of the motor nerves in addition to the sensory spinal nervous tissue.

Because the electrodes span several levels the generated stimulation energy 15 stimulates or is applied to more than one type of nerve tissue on more than one level. Moreover, these and other conventional, non-specific stimulation systems also apply stimulation energy to the spinal cord and to other neural tissue beyond the intended stimulation targets. As used herein, non-specific stimulation refers to the fact that the stimulation energy is provided to all spinal levels including the nerves and the spinal cord generally and indiscriminately. Even if the epidural electrode is reduced in size to simply stimulate only one level, that electrode will apply stimulation energy Indiscriminately to everything (i.e. all nerve fibers and other tissues) within the range of the applied energy. Moreover, larger epidural electrode arrays may after cerebral spinal fluid flow thus further altering local neural excitability states.

Another challenge confronting conventional neurostimulation systems is that since epidural electrodes must apply energy across a wide variety of tissues and fluids (i.e. CSF fluid amount varies along the spine as does pia mater thickness) the amount of stimulation energy needed to provide the desired amount of neurostimulation is difficult to precisely control. As such, increasing amounts of energy may be required to ensure sufficient stimulation energy reaches the desired stimulation area. However, as applied stimulation energy increases so too increases the likelihood of deleterious damage or stimulation of surrounding tissue, structures or neural pathways.

Improved stimulation devices, systems and methods are desired that enable more precise and effective delivery of stimulation energy. Such devices should be reliably manufactural, appropriately sized, cost effective and easy to use. At these some of these objectives will be fulfilled by the present invention.

SUMMARY

The present invention provides devices, systems and methods for stimulation of tissues and structures within a body of a patient. In particular, implantable leads are provided which are flexible, reliable and easily manufacturable for a variety of medical applications. Such leads are particularly suitable for stimulation of the spinal anatomy, more particularly suitable for stimulation of specific nerve anatomies, such as the dorsal root (optionally including the dorsal root ganglion). Such specificity is enhanced by the design attributes of the leads.

The implantable leads of the present invention utilize a flexible circuit. Typically, the flexible circuit includes an array of conductors bonded to a thin dielectric film. Example dielectric films include polyimide, polyvinylidene fluoride (PVDF) or other biocompatible materials to name a few. The conductors are comprised of biocompatible conductive metal(s) and/or alloy(s), such as gold, titanium, tungsten, titanium tungsten, titanium nitride, platinum, iridium, or platinum-iridium alloy, which is plated onto the dielectric film. The base and metal construct is then etched to form a circuit (i.e. an electrode pad contact and a "trace" to connect the pad to a connector). In some embodiments, redundancy in the "traces" is provided by utilizing multiple traces to the same contact to improve reliability.

Some advantages of leads comprised of a flexible circuit over traditional leads are greater reliability, size and weight reduction, elimination of mechanical connectors, elimination of wiring errors, increased impedance control and signal quality, circuit simplification, greater operating temperature range, and higher circuit density. In addition, lower cost is another advantage of using flexible circuits. In some embodiments, the entire lead will be formed from a flexible circuit. Also, in some embodiments, the lead will include an integrated connector for connection to an electronics package.

One main advantage of the flexible circuitry lead is its thinness and therefore flexibility. The thickness of the dielectric film typically ranges from 7.5 to 125 .mu.m (0.3 to 5 mils). However, in some embodiments, the lead will be comprised of a flexible circuit having a base layer of 0.5 to 2 mils thick.

The flexible circuitry used in the present invention may be single-sided, double-sided, or multilayer. Single-sided circuits are comprised of a single conductive layer and are the simplest type of flexible circuit. In some instances, a technique known as back baring or double access may be used to create a special type of single layer circuit. This technique allows access to the metal conductors from both sides of the circuit and is used when component soldering or other interconnection is desired on two sides of the circuit.

Double-sided circuits, as the name implies, are circuits with two conductive layers that are usually accessible from both sides. Multilayer refers to two or more layers which have been stacked and bonded.

In some embodiments, the flexible circuit is created with methods of the present invention. For example, metal deposition, such as vapor deposition, sputtering techniques or plasma fields, is used to coat the film structure with metal to form the electrodes and traces. In such embodiments, the film structure is comprised of polyvinylidene fluoride (PVDF). The process may utilize PVDF in either sheet form or, preferably, in roll form, with cooling to reduce thermal stresses between the dielectric film structure and the metal coat. The PVDF is coated with an adhesion layer, such as titanium or titanium-tungsten alloy, which will improve the reliability of the bond between the dielectric film structure and the electrodes and traces that will be deposited thereon. The adhesion layer is then coated, such as sputter coated, with a seed layer of conductive biocompatible metal, such as gold or platinum. After such metallization, the seed layer is patterned, either by photolithography and wet etch, or by laser ablation to form the shapes of the traces and electrodes. After patterning the seed layer of metal, sputtering or electroplating is used to increase the thickness of the traces in order to improve conductivity, and then again to create the final electrode working surface. Possible trace materials include platinum, gold, iridium-oxide, a combination thereof or any other conductive biocompatible metal suitable for implantation. The electrode surface may be coated over the entire metallization of the lead, or selectively and only over the intended electrode surface with an inert metal such as platinum, iridium-oxide, or combination thereof. In some embodiments, the adhesion layer of titanium or titanium-tungsten alloy is sputter coated with a seed layer of gold, then sputter coated with platinum and then electroplated with platinum. In other embodiments, the adhesion layer of titanium or titanium-tungsten alloy is sputter coated with a seed layer of gold, then electroplated with gold and then electroplated with platinum. In yet other embodiments, the adhesion layer of titanium or titanium-tungsten alloy is sputter coated with a seed layer of platinum, then electroplated with platinum. It may be appreciated that other combinations may also be used.

In a first aspect of the present invention, a method is provided for stimulating a tissue within a body. In some embodiments, the method comprises positioning a lead comprising a flexible circuit having at least one electrode so that at least one of the at least one electrode is disposed near a dorsal root. Optionally, the positioning ensures that at least one of the at least one electrode is disposed near a dorsal root ganglion of the dorsal root. The method also includes supplying electrical energy to the at least one of the at least one electrode so as to stimulate at least a portion of the dorsal root. In some embodiments, the portion of the dorsal root comprises a dorsal root ganglion.

Optionally, the method may include advancing the lead through a foramen and/or advancing the lead through an epidural space. Typically, the method further comprises joining the lead with an implantable pulse generator. In such instances, the method typically includes implanting the lead and the implantable pulse generator wholly within the body.

In a second aspect of the present invention, a flexible circuit lead is provided for stimulating a body tissue. In some embodiments, the lead comprises an elongate structure having a distal end configured to be positioned near a dorsal root and a proximal end coupleable with a pulse generator, wherein the structure comprises a dielectric film. The lead also includes at least one electrode disposed near the distal end and at least one conductive trace extending from the at least one electrode toward the proximal end so that stimulation energy is transmittable from the coupled pulse generator to the at least one electrode so as to stimulate the at least a portion of the dorsal root.

In some embodiments, the at least one electrode is comprised of a biocompatible conductive metal, alloy or combination of these plated onto the dielectric film. In such instances, the biocompatible conductive metal, alloy or combination may include gold, titanium, tungsten, titanium tungsten, titanium nitride, platinum, iridium or platinum-iridium alloy. Often, the dielectric film has a thickness in the range of approximately 7.5 to 125 .mu.m.

In some embodiments, the at least one electrode comprises a plurality of electrodes arranged substantially linearly along a longitudinal axis of the distal end. In other embodiments, the at least one electrode comprises a plurality of electrodes arranged substantially linearly along a horizontal axis of the distal end. Optionally, the at least one electrode comprises a plurality of electrodes arranged in a substantially circular or arc shape.

In some instances, the distal end has a pronged shape including at least two prongs. In such instances, one of the at least one electrodes may be disposed near a tip of one of the at least two prongs. In some embodiments, the distal end is configured to wrap around the body tissue. And typically, the distal end of the elongate structure is passable through a needle.

In a third aspect of the present invention, a lead is provided for stimulating a body tissue comprising: an elongate structure having a proximal end coupleable with a pulse generator and a distal end having two edges which are capable of being positioned in opposition, wherein the distal end includes at least two electrodes which generally oppose each other when the edges are positioned in opposition so as to stimulate the body tissue. Typically the body tissue comprises a dorsal root ganglion.

In some embodiments, the distal end forms a V-shape or U-shape when the two edges are positioned in opposition which allows the body tissue to be positioned at least partially within the V-shape or U-shape. The distal end may comprise two elongate elements, each element having one of the two edges. In such instances, the two elongate elements may be positionable in linear alignment with a longitudinal axis of the elongate structure.

In some embodiments, the distal end has a rounded shape wherein sides of the rounded shape form the two edges. In such embodiments, the sides of the rounded shape may curl or fold towards each other to position the two edges in opposition.

Typically, the elongate structure comprises a dielectric film. The dielectric film may have a thickness in the range of approximately 7 to 125 .mu.m. Also, the at least two electrodes may be comprised of a biocompatible conductive metal, ahoy or combination of these plated on the dielectric film. Typically, the distal end is passable through a needle.

In another aspect of the present invention, a system for stimulating a body tissue is provided comprising: a first elongate structure having first proximal end coupleable with a pulse generator and a first distal end, wherein the first distal end has a first inner surface having a first electrode disposed thereon, and a second elongate structure having a second proximal end coupleable with the pulse generator and a second distal end, wherein the second distal end has a second inner surface having a second electrode disposed thereon. The first and second elongate structures are joined so that the first and second electrodes are capable of directing stimulation energy toward each other, and wherein the first and second distal ends are moveable away from each other so as to allow the body tissue to be positioned at least partially therebetween to receive the stimulation energy.

In some embodiments, the first and second elongate structures are slidably joined. Optionally, the first distal end is movable by recoil force. In some systems, the first distal end is attachable to a first obturator which is capable of moving the first distal end. In these systems, the first obturator may be configured to dissect tissue while it moves the first distal end. Optionally, the first obturator may be advanceable from a delivery device so as to advance the first distal end and move the first distal end away from the second distal end.

Typically, the first elongate structure comprises a dielectric film. And, typically, the body tissue comprises a dorsal root ganglion. Optionally, the distal end may be passable through a needle.

In some embodiments, the first elongate structure includes a first contact pad disposed on an outer surface of the proximal end of the first elongate structure, wherein the first contact pad provides electrical connection from the first electrode to the pulse generator. And in some embodiments, the second elongate structure includes a second contact pad disposed on an outer surface of the proximal end of the second elongate structure, wherein the second contact pad provides electrical connection from the second electrode to the pulse generator.

In another aspect of the present invention, a flexible circuit lead is provided for stimulating a body tissue, wherein the lead comprises an elongate structure having a distal end comprising at least one electrode on a dielectric film, and wherein the distal end is movable to at least partially surround the body tissue and direct stimulation energy from the at least one electrode toward the body tissue. Typically, the distal end is passable through a needle.

In some embodiments, the distal end is moveable by curling or uncurling so as to at least partially surround the body tissue. In other embodiments, the distal end is moveable by folding or unfolding so as to at least partially surround the body tissue.

Typically, the distal end comprises opposing elements which move toward or away from each other so as to at least partially surround the body tissue. In some instances, the opposing elements may move independently. Optionally, the opposing elements may form a V-shape.

In another aspect of the present invention, a device is provided for stimulating a body tissue, wherein the device comprises an elongate shaft having an outer surface and a lead having a at least one electrode, wherein the lead is mounted on the outer surface of the elongate shaft so that the at least one electrode is positionable near a dorsal root for stimulation. Typically, the lead is comprised of an elongate structure comprising a dielectric film. In such instances, the at least one electrode may be comprised of a biocompatible conductive metal, alloy or combination of these plated onto the dielectric film.

In some embodiments, the elongate shaft includes a lumen therethrough configured for passage of a stylet. In some embodiments, the at least one electrode comprises a plurality of electrodes positioned so as to wrap at least partially around the elongate shaft. And in some embodiments, the elongate shaft is configured for implantation in an arrangement so that the at least one electrode is positioned near a dorsal root ganglion.

In yet another aspect of the present invention, a lead is provided for stimulating a body tissue, wherein the lead comprises a first elongate structure having a first distal end configured to be positioned near the body tissue and a first proximal end coupleable with a pulse generator. The first elongate structure has a first electrode disposed near the first distal end. The lead also includes a second elongate structure having a second distal end, a second proximal end and a second electrode disposed near the second distal end. The second elongate structure is attached to the first elongate structure in a layered configuration so that stimulation energy is transmittable from the coupled pulse generator to the first and second electrode so as to stimulate the body tissue.

In some embodiments, the layered configuration offsets the distal ends. In some embodiments, the first and second electrodes are arranged substantially linearly along a longitudinal axis of the distal end.

In some instances, the lead further comprises a third elongate structure having a third proximal end, a third distal end and a third electrode disposed near the third distal end, wherein the third elongate structure is attached to the second elongate structure in a layered configuration so that stimulation energy is transmittable from the coupled pulse generator to the third electrode so as to stimulate the body tissue. Typically, the distal ends of the layered configuration of elongate structures are passable through a needle.

In some embodiments, the at least one conductive trace extends from each electrode toward its respective proximal end. In such embodiments, each conductive trace may have a shape so that the layered configuration balances the conductive traces. At least one of the at least one conductive traces may have a zig-zag or serpentine shape.

Typically, the first elongate structure comprises a dielectric film. In such instances, the first electrode is comprised of a biocompatible conductive metal, alloy or combination of these plated onto the dielectric film. Optionally, the biocompatible conductive metal, alloy or combination includes gold, titanium, tungsten, titanium tungsten, titanium nitride, platinum, iridium or platinum-iridium alloy.

Other objects and advantages of the present invention will become apparent from the detailed description to follow, together with the accompanying drawings.

BRIEF DESCRIPTION OF THE DRAWINGS

FIG. 1A-1B, 2, 3, 4, 5 illustrate prior art.

DETAILED DESCRIPTION

Figure 2:
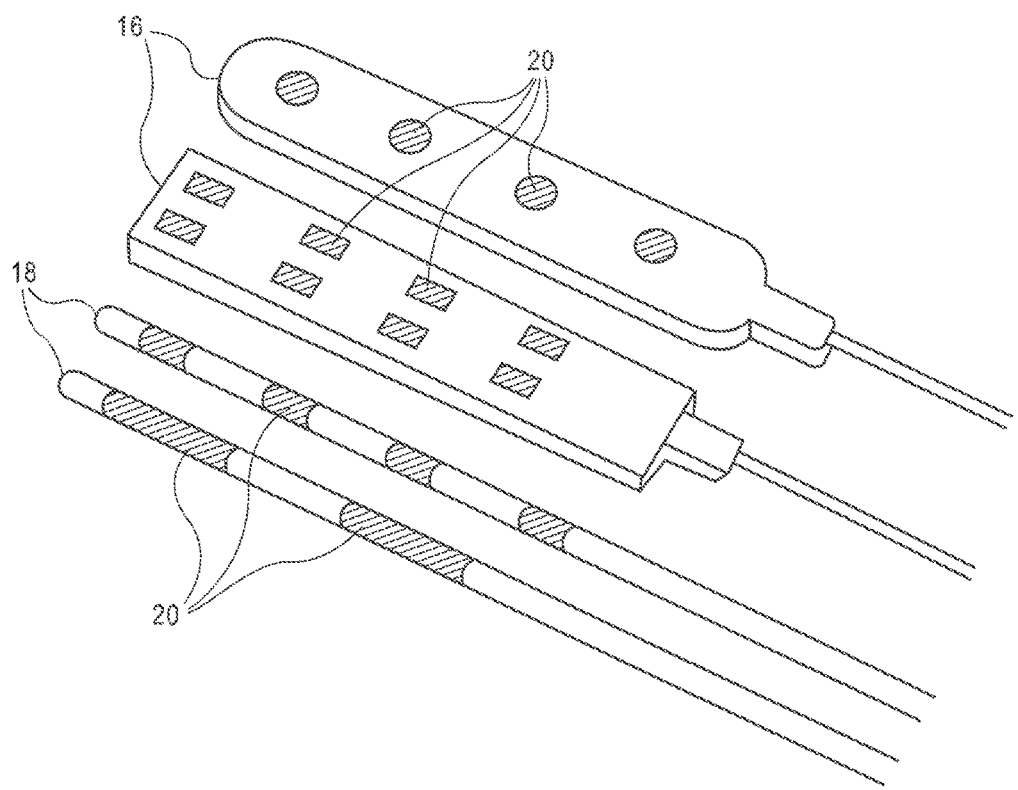
Figure 3:
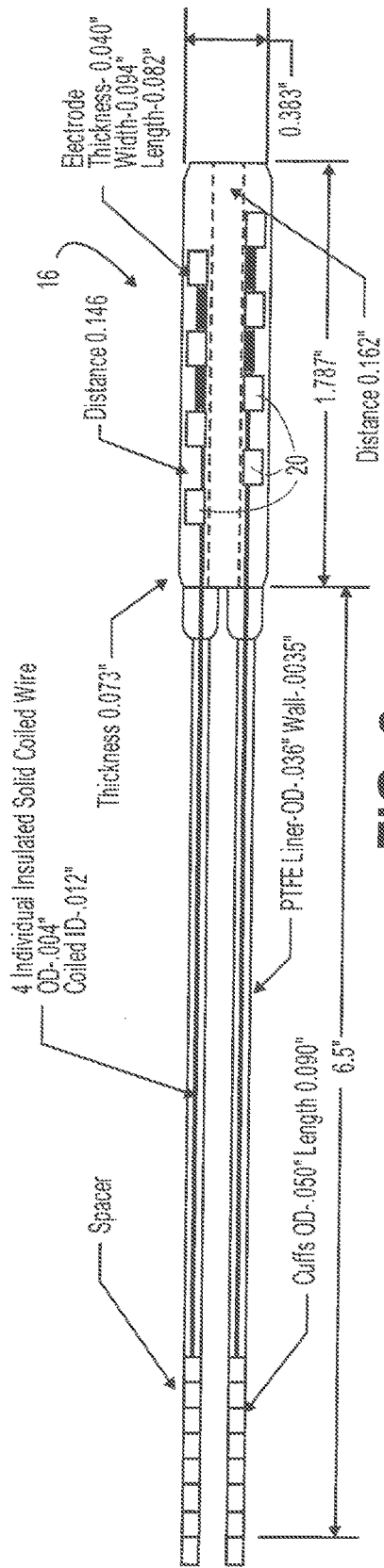
Figure 4:
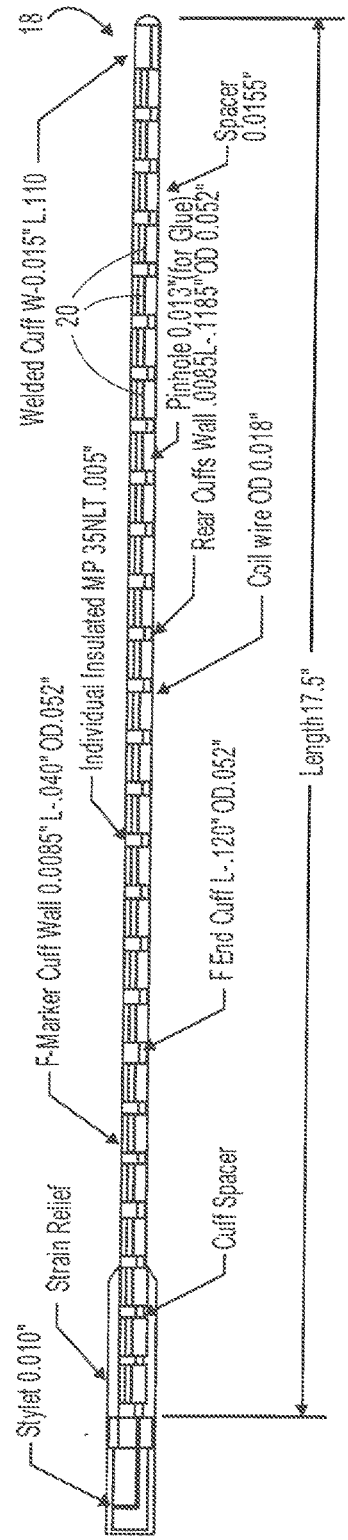
Figure 5:
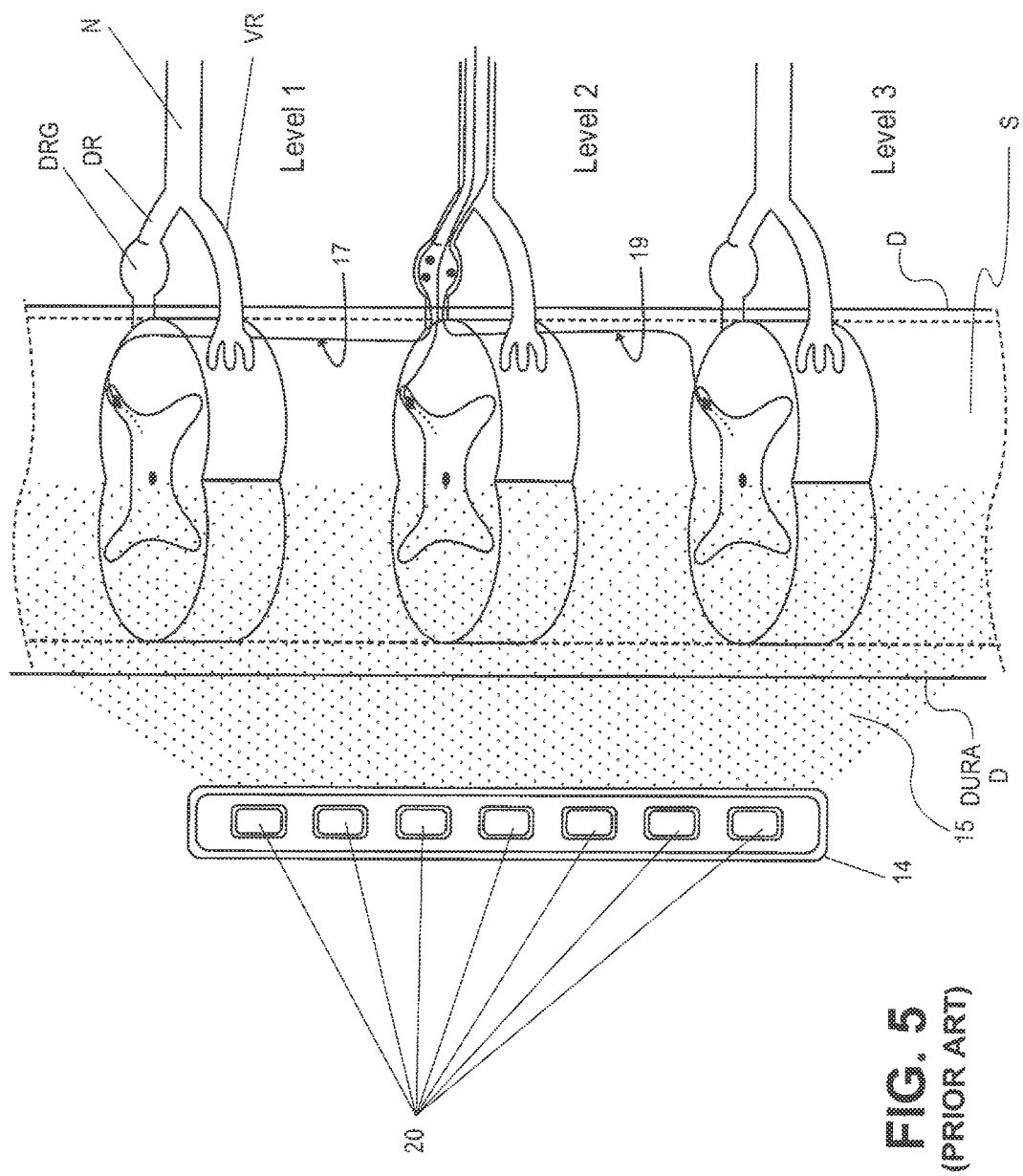
Figure 6A:
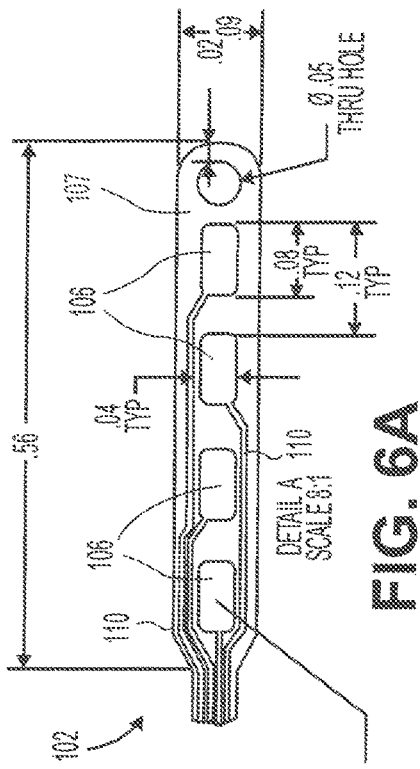
FIG. 6, 6A, 6B illustrates an embodiment of a flexible circuit lead of the present invention.
Figure 6B:
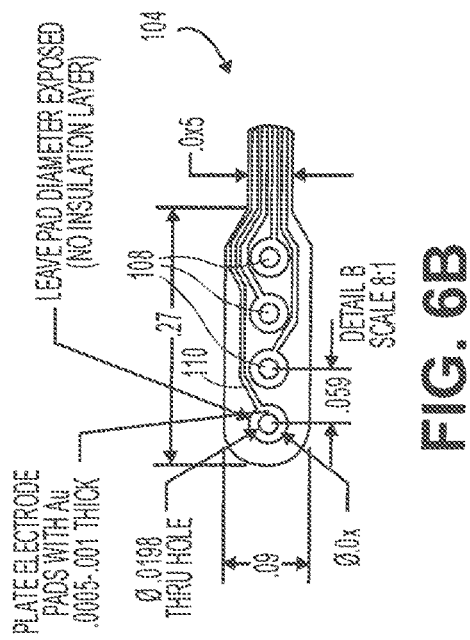
Figure 6:
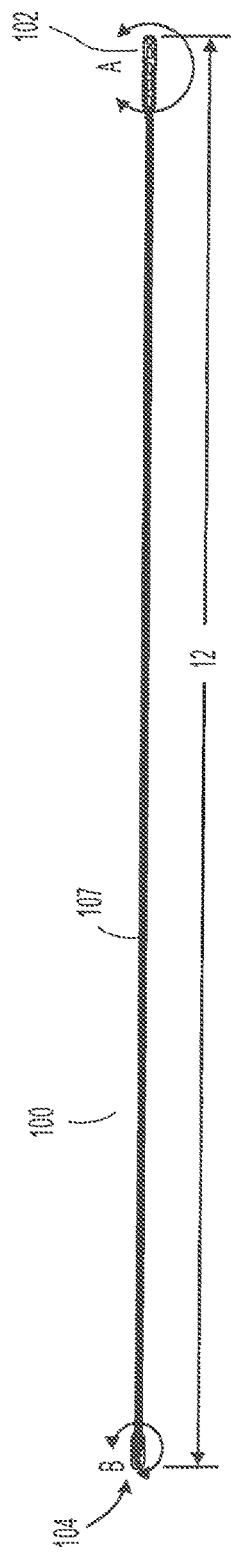

FIG. 6 illustrates an embodiment of a lead 100 of the present invention. The lead 100 is comprised of a flexible circuit. In particular, the lead 100 is comprised of an elongate structure 107 having a distal end 102 and a proximal end 104. The distal end 102 is configured to be positioned near a target body tissue and the proximal end 104 is coupleable with a power source or implantable pulse generator (IPG). FIG. 6A provides a detailed illustration of the distal end 102 of the lead 100 of FIG. 6. As shown, the lead 100 includes at least one electrode 106 plated on the dielectric film. In this embodiment, four electrodes 106 are present in an array. It may be appreciated that any number of electrodes 106 may be used in any desired arrangement, including longitudinally aligned individually (as shown) or in pairs or sets. FIG. 6B provides a detailed illustration of the proximal end 104 of the lead 100 of FIG. 6. The proximal end 104 includes contact pads 108 that are used to connect with the IPG. In this embodiment, four contact pads 108 are shown, one corresponding to each electrode 106. Each contact pad 108 is electrically connected with an electrode 106 through a conductive trace 110 that extends therebetween, thus from the proximal end 104 to the distal end 102. Stimulation energy is transmitted from the IPG through the contact pads 108 and through trace 110 to the electrodes 106 which stimulate the desired target tissue. It may be appreciated that in some embodiments, the conductive traces 110 are arranged so that each contact pad 108 is connected with more than one electrode 106 or each electrode 106 is connected with more than one contact pad 108.

Figure 7A:
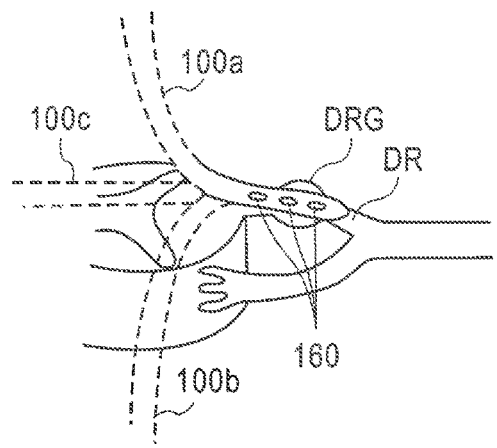
FIGS. 7A, 7B, 7C, 7D illustrate a variety of approaches to an example target anatomy for positioning the leads of the present invention.
Figure 7B:
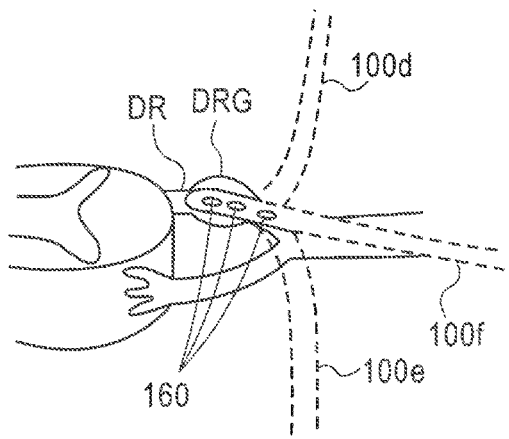
Figure 7C:
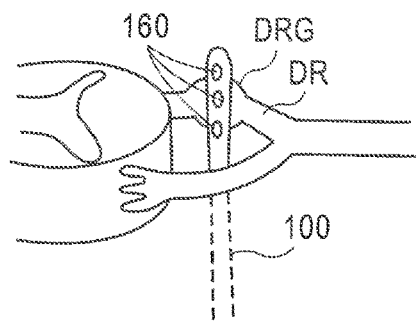
Figure 7D:
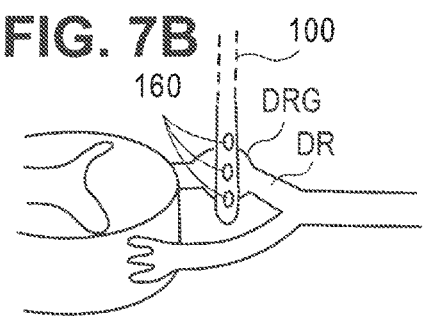

The leads 100 of the present invention may be used to stimulate a variety of target tissues, particularly a dorsal root ganglion DRG. FIGS. 7A-7D illustrate various approaches to the DRG and positioning a lead 100 of the present invention so as to stimulate the DRG. Embodiments of these approaches include passing through, near or along one or more posterior or lateral openings in the bony structure of the spinal column. An example of a posterior opening is an opening between adjacent spinous processes. An example of a lateral opening is the foramen or opening at least partially defined by the articulating processes and the vertebrae. FIG. 7A illustrates a retrograde (100a), antegrade (100b) and lateral approach (100c) to the dorsal root and DRG from the spinal column. FIG. 7B illustrates a retrograde (100d), antegrade (100e) and lateral approach (100f) to the dorsal root and OR from outside of the spinal column, such as from a side or traditional percutaneous approach. FIG. 7C illustrates an antegrade approach to a dorsal root and DRG between an articulating process (not shown) and the vertebral body (not shown). FIG. 7D illustrates a retrograde approach to a dorsal root and DRG between an articulating process (not shown) and a vertebral body (not shown). The leads of the present invention may also be positioned by any other suitable method or approach. One exemplary retrograde approach is a retrograde translaminar approach. One exemplary approach is an antegrade translaminar approach. One exemplary lateral approach is a transforamenal approach.

As mentioned above, each lead 100 includes at least one electrode 106, preferably two, three, four, five, six or more electrodes. The lead 100 is preferably aligned so that at least one of the at least one electrodes 160 is positioned as close to the target location as possible, for example, on the DRG. In some situations, the DRG has a size of 5-10 mm. Thus, in some embodiments, a lead 100 having four 1 mm square electrodes spaced 1-2 mm apart would allow all four of the electrodes to simultaneously contact the DRG. In such an instance, all four electrodes may provide stimulation energy. In other embodiments, the electrodes may be sized or shaped so that less than the total number of electrodes are desirably positioned on or near the target location. This may also occur due to placement of the lead. In such instances, a subset of the electrodes may provide stimulation energy, preferably one or more electrodes positioned closest to the target location. This assists in reducing or eliminating undesired stimulation of non-target anatomies.

Figure 8:
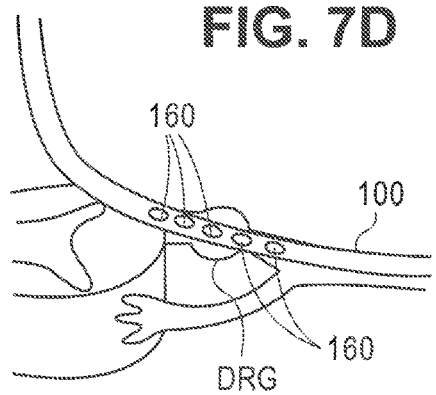
FIG. 8 illustrates electrodes positioned more proximal to the distal tip of the lead.

It may be appreciated that the electrodes may be positioned at any location along the length of the lead, may have any suitable shape and any suitable spacing. FIG. 8 illustrates electrodes 160 positioned more proximal to the distal tip of the lead 100. Thus, a portion of the lead 100 having no electrodes 160 extends distally beyond the last electrode 160. When the electrodes 160 are positioned over the target location, the distal most end of the lead 100 extends therefrom, such as transforamenally. Such extension may assist in anchoring the lead. It may be appreciated that the lead 100 of FIG. 8 may alternatively be positioned by any of the approaches listed above, or any other approaches.

Figure 9:
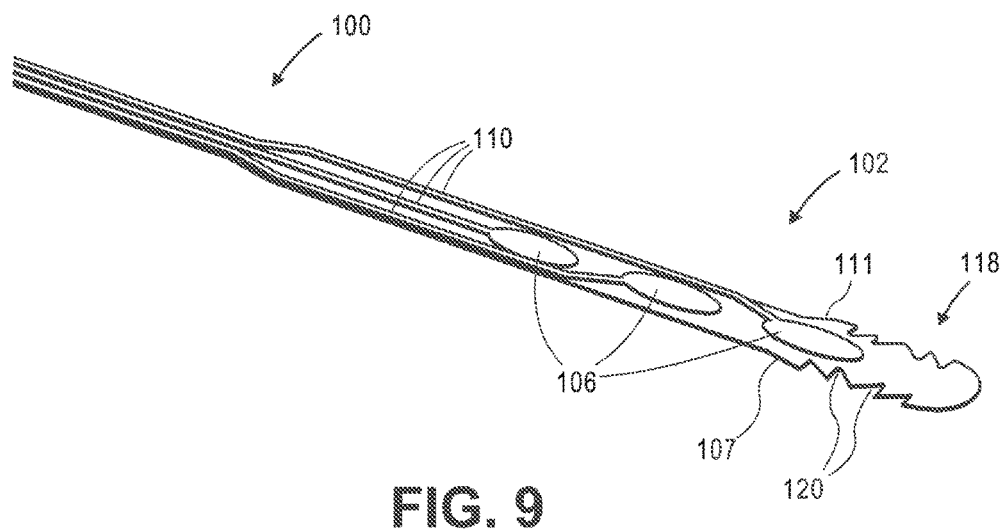
FIG. 9 illustrates a distal end of an embodiment of a flexible circuit lead of the present invention.

FIG. 9 illustrates a distal end 102 of another embodiment of a flexible circuit lead 100 of the present invention. In this embodiment, three electrodes 106 are disposed in an array on the film structure 107, each electrode 106 having a trace 110 which extends toward the proximal end 104 of the lead. In this embodiment, the lead 100 also includes an anchoring feature 118 which assists in anchoring the lead 100 within tissue to resist migration of the lead 100. In this embodiment, the anchoring feature 118 comprises a plurality of serrations or notches 120 cut into the film structure 107. The notches 120 may have any suitable shape, dimension or spacing. Likewise, the notches 120 may be symmetrical, non-symmetrical, present along one edge 111 of the film structure 107 or along more than one edge. In this embodiment, the anchoring feature 118 extends distally of the distal-most electrode 106, however it may disposed at any location along the lead 100.

Figure 10:
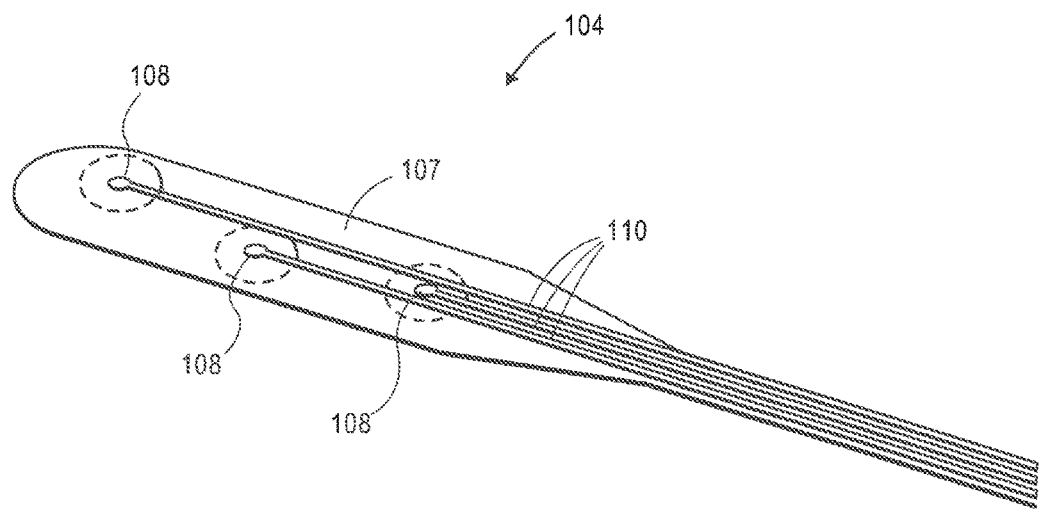
FIG. 10 illustrates a proximal end of an embodiment of a flexible circuit lead of the present invention.

FIG. 10 illustrates an example of a proximal end of the lead 100 corresponding to the distal end 102 of FIG. 9. Here, each of the three traces 110 terminate in a contact pad 108. Each contact pad 108 is then electrically connected with a connection terminal (as will be described in a later section) which transmits stimulation energy from the implanted IPG.

The thinness and flexibility of the dielectric film allow a variety of different types of leads 100 to be formed. Such types include layered leads, circular leads, leads which curl or wrap around target tissue, leads which fold and expand, leads which surround a target tissue, leads mounted on delivery devices and a variety of other leads designs suitable for stimulating specific types of target tissue, particularly a DRG.

Figure 11A:
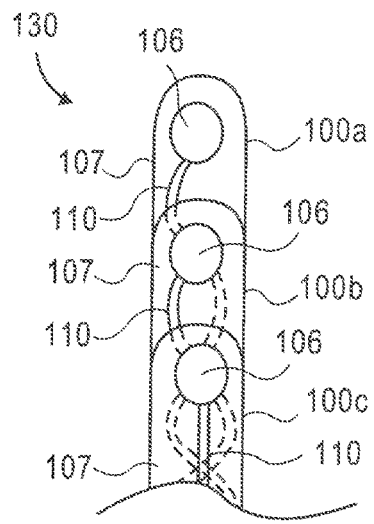
FIGS. 11A-11B illustrate a layered lead comprising two or more individual leads which are layered and bonded together.
Figure 11B:
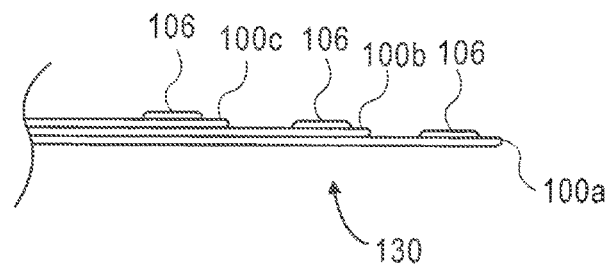

FIGS. 11A-11B illustrate an embodiment of a layered lead 130. A layered lead 130 comprises two or more individual leads which are layered and bonded together. FIG. 11A shows three individual leads 100a, 100b, 100c, each comprising a film structure 107 having an electrode 106 disposed thereon and a trace 110. It may be appreciated that each individual lead may alternatively have a plurality of electrodes disposed thereon, such as in an array. The three leads 100a, 100b, 100c are staggered so that the electrodes 106 are exposed and facing the same direction. In this embodiment, the traces 110 are positioned so that when the leads are layered, the traces 110 are balanced across the layered lead 130. For example, the traces 110 may have opposing zig-zag or serpentine shapes when layered. This improves flexibility and handling characteristics of the lead 130. FIG. 1B provides a side-view of the layered lead 130 of FIG. 11A. Such layering allows each individual lead more surface area, such as for redundant traces 110 for each electrode 106. Since the leads are so thin, layering of the leads is still very thin and flexible. In addition, insulation layers may be bonded between one or more of the individual leads. In some embodiments, the proximal end of the layered lead is layered in a mirrored fashion so that each of the contact pads are exposed.

Figure 12:
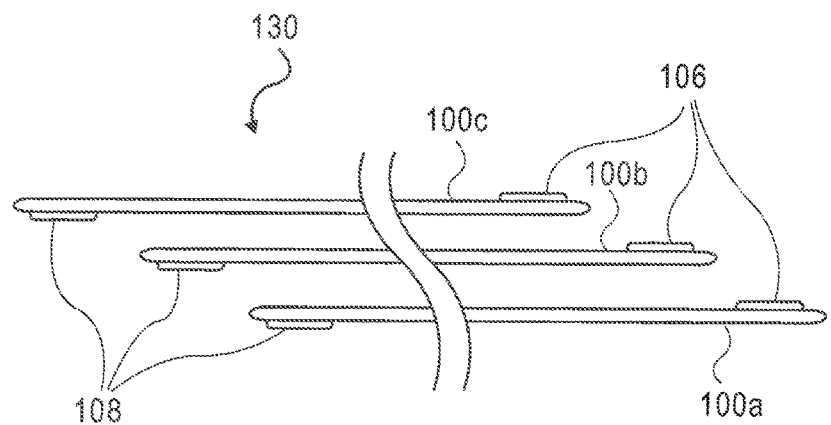
FIG. 12 illustrates an embodiment of a layered lead in an expanded view.

FIG. 12 illustrates an embodiment of a layered lead 130 in an expanded view. The three leads 100a, 100b, 100c are staggered so that the electrodes 106 are exposed and facing the same direction. In this embodiment, the contact pads 108 are disposed on an opposite side of each of the leads 100a, 100b, 100c. This provides for the contact pads 108 to also be exposed and facing the same direction when the leads are layered.

Figure 13:
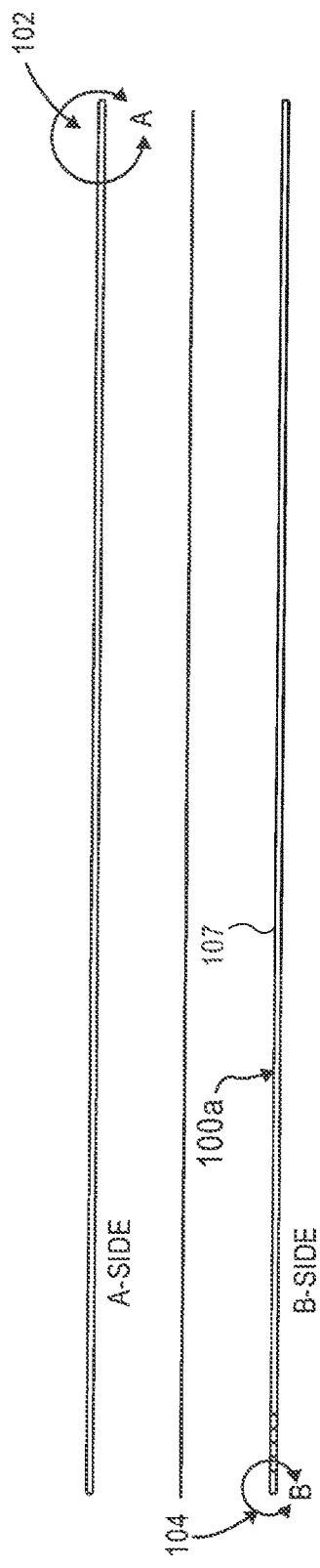
FIGS. 13, 13A, 13B illustrates an example of a lead which may be used in layering.
Figure 13A:
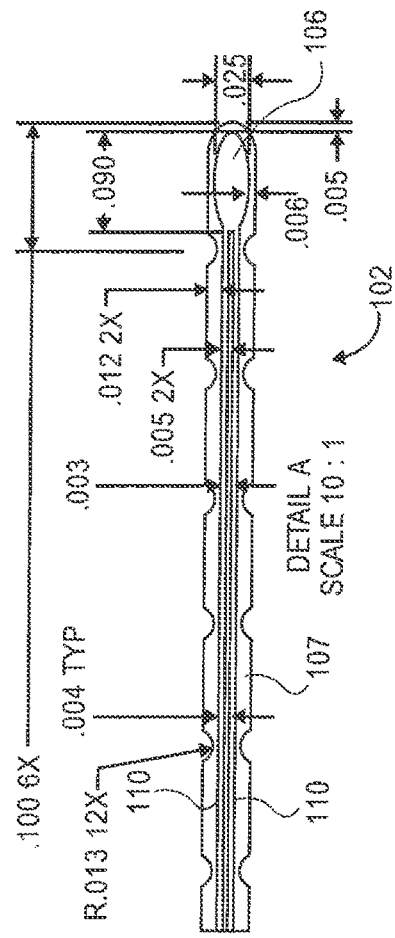
Figure 13B:
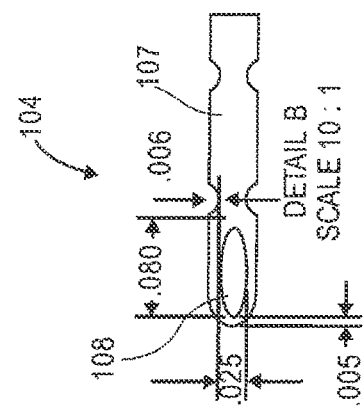

FIG. 13 illustrates an example of a lead, such as lead 100a, which may be used in layering. The lead 100a comprises an elongate film structure 107 having a distal end 102 and a proximal end 104. FIG. 13A provides a detailed illustration of the distal end 102 of the lead 100 of FIG. 13. As shown, the lead 100a includes at least one electrode 106 plated on the "A-side" of the dielectric film structure 107. In this embodiment, one electrode is present FIG. 13B provides a detailed illustration of the proximal end 104 of the lead 100a of FIG. 13. The proximal end 104 includes a contact pad 108 on the "B-side" of the film structure 107 which is used to connect with the IPG. In this embodiment, a circuit trace 110 extends from the electrode 106, along the "A-side" of the structure 107, through a via to the "B-side" of the structure 107 and connects with the contact pad 108. Thus, when a plurality of such leads are layered, as in FIG. 12, stimulation energy may be transmitted from each of the staggered contact pads 108, through the associated traces, to the associated staggered electrodes 106 to stimulate the desired target tissue.

Figure 14:
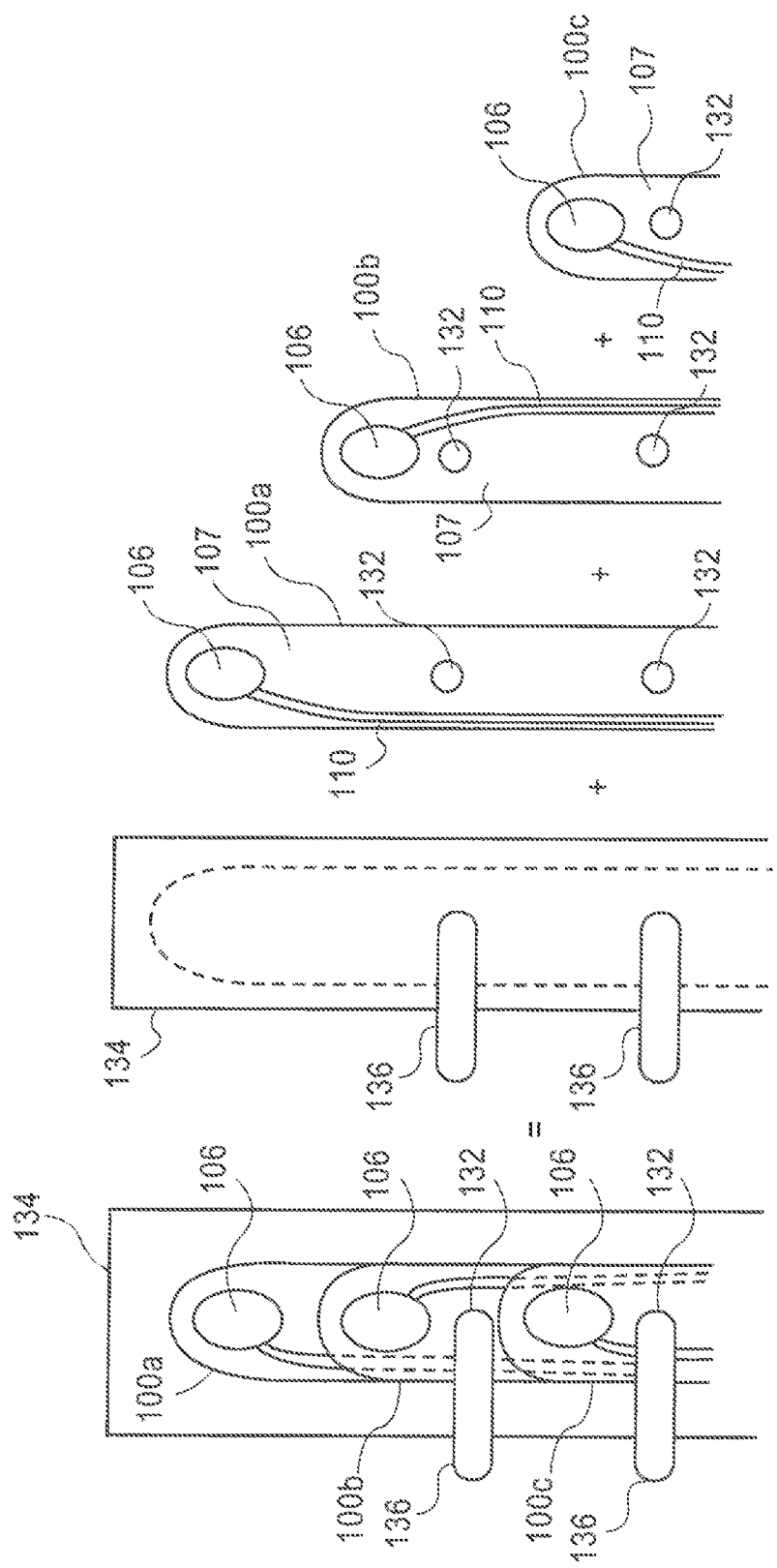
FIG. 14 illustrates an example process and fixture for forming a layered lead.

FIG. 14 illustrates an example process and fixture for forming a layered lead 130. Three individual leads 100a, 100b, 100c are shown, each comprising a film structure 107 having an electrode 106 disposed thereon and a trace 110. In this embodiment, each lead 100a, 100b, 100c is of the same length, however differing sized portions are shown for clarity. In addition, each lead 100a, 100b, 100c has an alignment hole 132. The alignment holes 132 are used to assist in consistently and precisely aligning the leads in a layered arrangement. A fixture 134 is shown having one or more posts 136 positioned thereon. The posts 136 are sized and arranged so that the posts 136 are passable through the alignment holes 132 when the leads 100*a*, 100*b*, 100*c* are placed thereon. Once the leads 100*a*, 100*b*, 100*c* are desirably positioned, the leads are bonded and fixed in this arrangement. The layered lead 130 may then be removed from the fixture 134. In some embodiments, the resulting alignment holes 132 may be used for other purposes, such as for suturing a portion of the layered lead 130 to tissue during implantation.

Figure 15A:
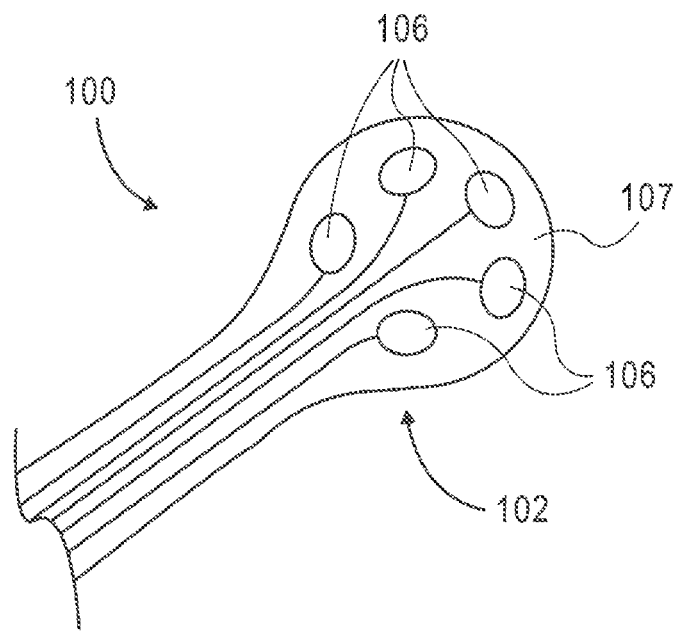
FIG. 15A illustrates a lead of the present invention having an oval, rounded or circular distal end.
Figure 15B:
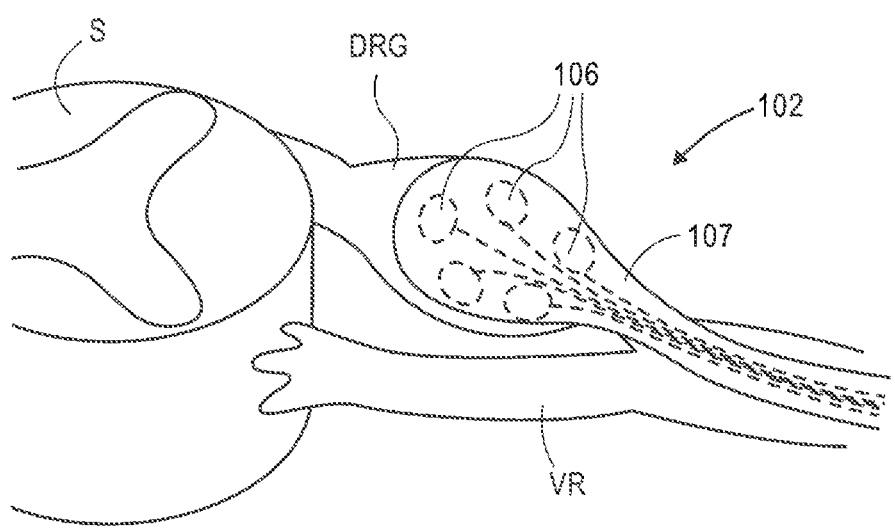
FIG. 15B illustrates the lead of FIG. 15A positioned so that its distal end is in proximity to a dorsal root ganglion.

It may be appreciated that the flexible circuit leads 100 may have a variety of shapes, sizes and dimensions. In particular, the distal end 102 may be shaped to provide a particular electrode placement or to conform to a particular anatomy. For example, FIG. 15A illustrates a lead 100 of the present invention having an oval, rounded or circular distal end 102. Here, the film structure 107 is formed into the oval, rounded or circular shape and the electrodes 106 are arranged therearound, such as in a circular or arc pattern. This arrangement may provide a particularly desirable stimulation area or may more easily target a particular tissue, such as a dorsal root ganglion OR which may have a circular or oval shape. FIG. 15B illustrates the lead 100 of FIG. 15A positioned so that its distal end 102 is in proximity to a DRG. As shown, the distal end 102 is positioned over the DRG so that its circular shape substantially aligns with the circular shape of the DRG. The lead 100 is positioned so that the electrodes 106 face the DRG, and are therefore represented in dashed line. Appropriate electrodes may then be selected for stimulation of the DRG based on desired pain relief. In some instances, the circular shape increases the number of electrodes 106 able to be used for stimulation and promotes selective stimulation of the DRG.

Figure 16A:
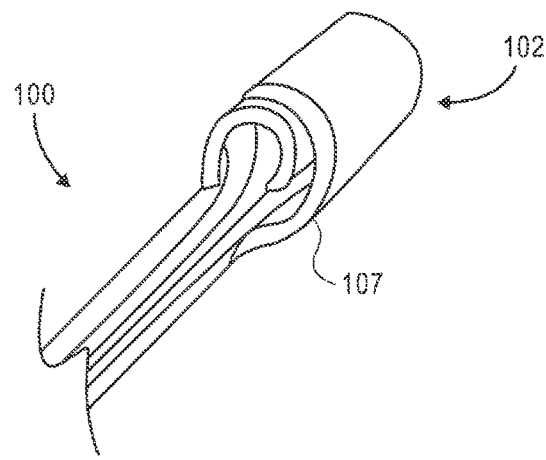
FIGS. 16A, 16B, 16C illustrate a distal end of a lead which is curlable or rollable.
Figure 16B:
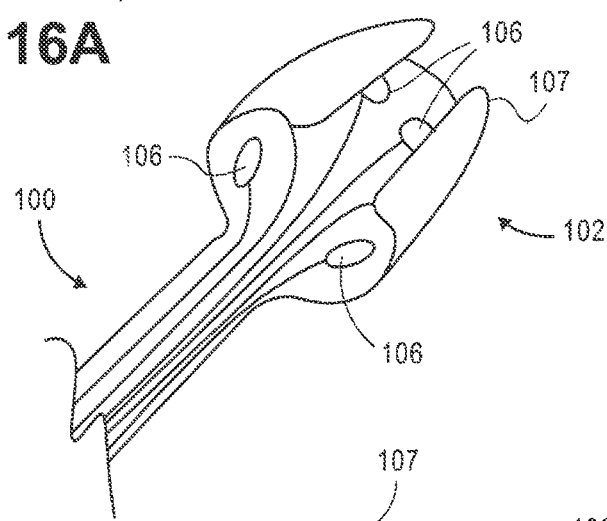
Figure 16C:
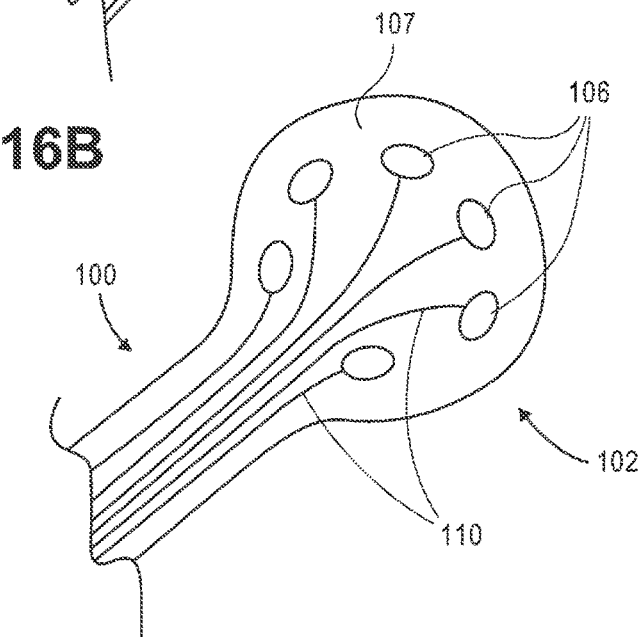

In addition, the film structure 107 may be curled or rolled for ease of delivery and/or to wrap around a target tissue area. FIG. 16A illustrates the distal end 102 rolled into a cylindrical shape. Such a cylindrical shape may easily fit within a cylindrically shaped delivery catheter or device. Thus, the lead 100 may be advanced from the delivery device in a rolled orientation wherein it may be deployed to an at least partially unrolled state. FIG. 16B illustrates the distal end 102 partially unrolled and FIG. 16C illustrates the distal end 120 in an unrolled, flat orientation. In an at least partially unrolled state, the distal end 102 may fully or partially wrap around a target tissue (such as the DRG or including the DRG). In this configuration, the electrodes face each other having the target tissue therebetween. Appropriate electrodes may then be selected for stimulation of the tissue area therebetween based on patient interview for best relief of pain. In some embodiments, one or more obturators may be used to assist in unrolling and positioning of the circular lead 100.

Figure 17:
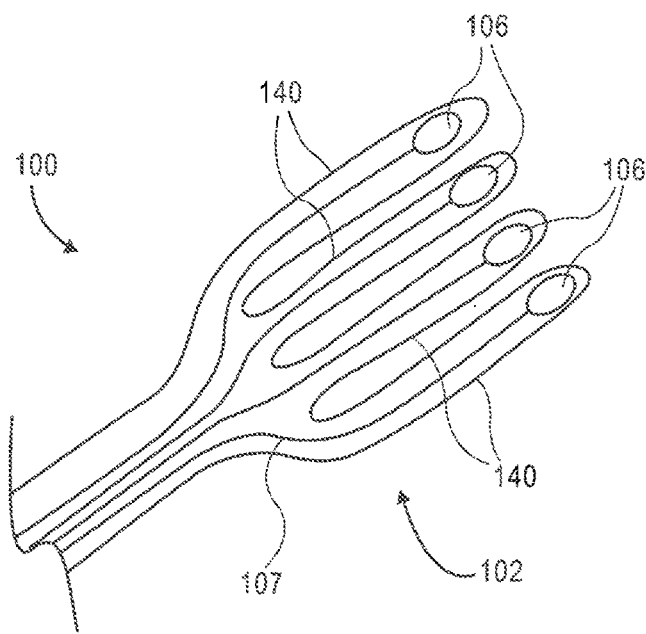
FIG. 17 illustrates a lead of the present invention having a pronged distal end.
Figure 18:
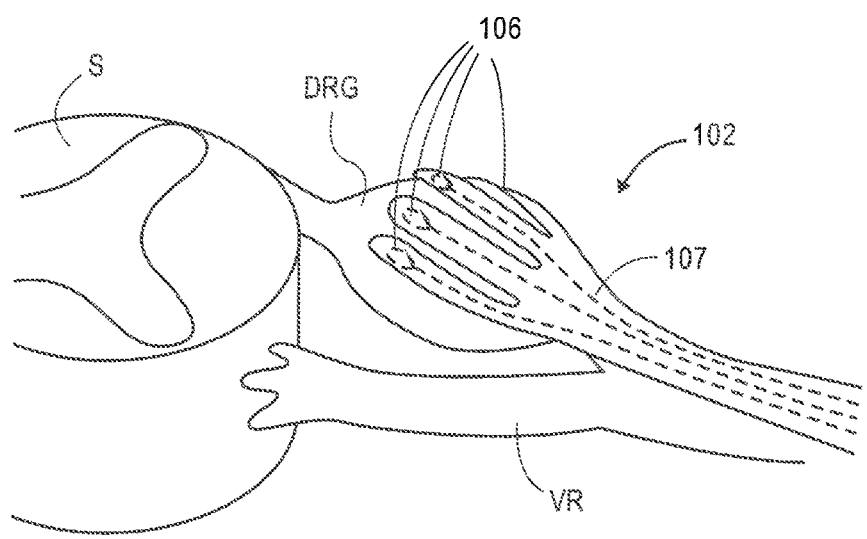
FIG. 18 illustrates the lead of FIG. 17 positioned so that its distal end is in proximity to a dorsal root ganglion.

FIG. 17 illustrates a lead 100 of the present invention having a pronged distal end 102. Here, the film structure 107 is shaped to provide a plurality of elongate prongs 140, each prong 140 having an electrode 106 positioned thereon. The prongs 140 may wrap around a delivery catheter or around a portion of the anatomy during implantation. For example, FIG. 18 illustrates the lead 100 of FIG. 17 positioned so that its distal end 102 is in proximity to a DRG. As shown, the distal end 102 is positioned over the DRG and at least some of the prongs 140 wrap around the DRG. The lead 100 is positioned so that the electrodes 106 face the DRG, and therefore represented in dashed line. Appropriate electrodes may then be selected for stimulation of the DRG based on desired pain relief. In some instances, the pronged shape increases the number of electrodes 106 able to be used for stimulation and promotes selective stimulation of the DRG.

Figure 19:
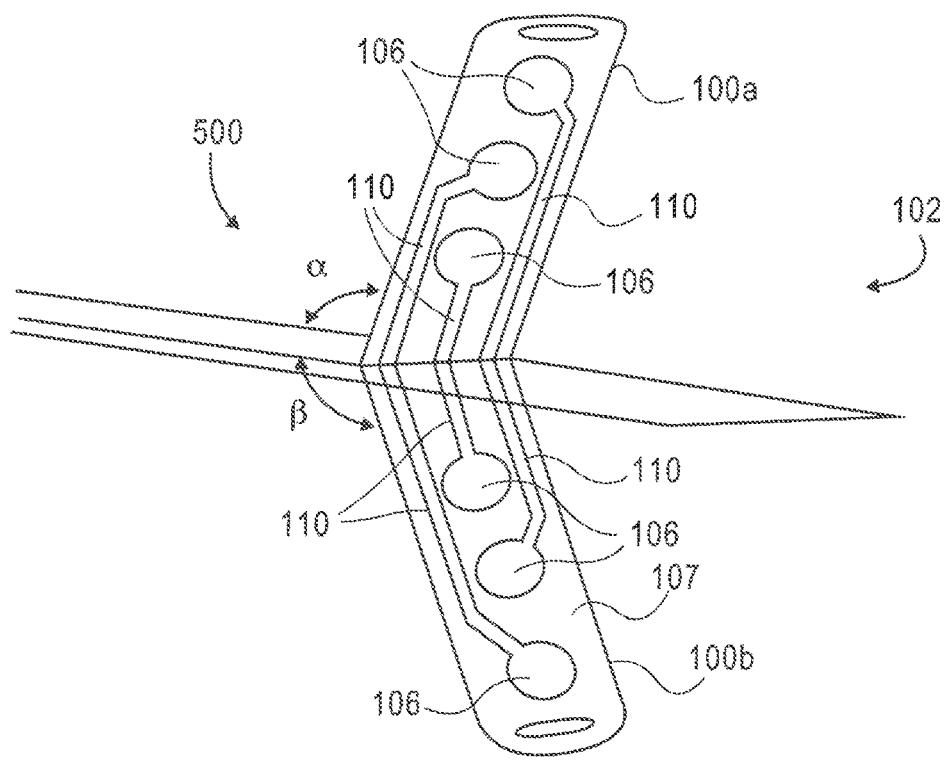
FIGS. 19-20 illustrate an embodiment of a shaped flexible circuit lead which can form a three dimensional shape.
Figure 20:
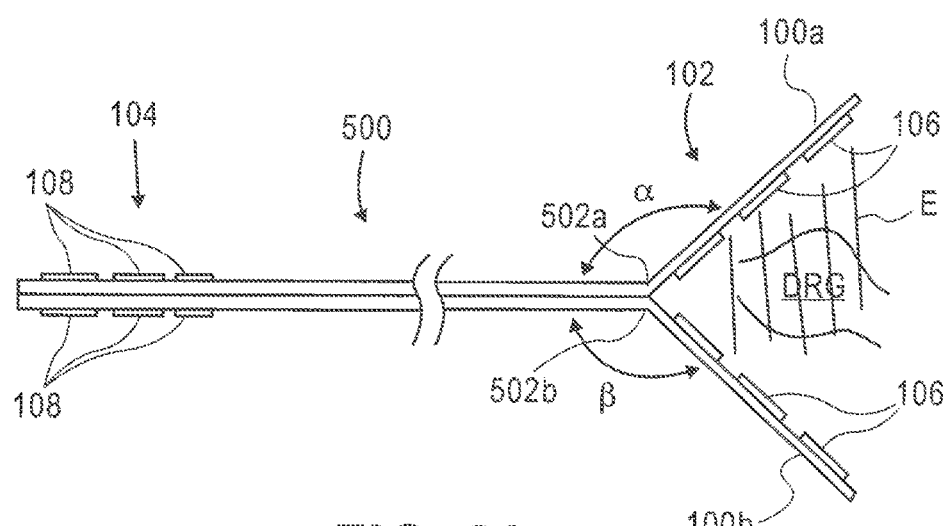

It may be appreciated that the film structure 107 is not only bendable and flexible, but also foldable and creasable. Thus, the leads 100 can form a variety of three-dimensional shapes which assist in wrapping around particular tissues and anatomies. FIGS. 19-20 illustrate an embodiment of a shaped flexible circuit lead 500 of the present invention. The shaped lead 500 is comprised of two individual leads 100*a*, 100*b*, each having at least one electrode 106 along one side of its distal end 102 and at least one corresponding contact pad 108 along the opposite side of its proximal end 104. Thus, the electrodes 106 and the contact pads 108 reside on opposite sides of each individual lead 100*a*, 100*b*. Lead 100*a* is folded to form a crease 502*a* along its length between the electrodes 106 and the contact pads 108 so that an acute angle .alpha. is formed between the back of the distal end (opposite the electrodes 106) and the face of the proximal end 104 having the contact pads 108 thereon. Likewise, lead 100*b* is folded to form a crease 502*b* along its length between the electrodes 106 and the contact pads 108 so that an acute angle .beta. is formed between the back of the distal end (opposite the electrodes 106) and the face of the proximal end 104 having the contact pads 108 thereon. The angles .alpha., .beta. may be the same or different. The leads 100*a*, 100*b* are assembled so that the creases 502*a*, 502*b* are aligned and the angles .alpha., .beta. face away from each other, as shown. Consequently, the distal ends of the leads 100*a*, 100*b* form a V shape wherein the electrodes 106 face each other within the mouth of the V. The leads 100*a*, 100*b* may optionally be bonded together to maintain this shaped lead 500. Alternatively, the leads 100*a*, 100*b* may reside in this arrangement, allowing the leads to slide in relation to each other to adjust position.

FIG. 20 illustrates the shaped lead 500 wrapped around a target tissue area, including a target DRG. As shown, the lead 500 is positioned so the target tissue area resides between at least a portion of the electrodes 106 along the mouth of the V. Thus, stimulation energy E provided by the electrodes 106, is provided to the tissue area laying therebetween (within the V). This provides a higher likelihood of stimulating the target DRG, since the exact location of the DRG within the target tissue area may not be known.

Positioning of the contact pads 108 on opposite sides of the assembled shaped lead 500 allows the joined proximal end 104 to easily be connected to a connector (such as in a quick connect arrangement) which is in turn connected with an IPG to supply the stimulation energy E.

It may be appreciated that other shapes may be formed, such as a "J" shape. Or, a triangular shaped lead may be formed having three distal end portions (forming a tripod shape). When deployed, this may covering a larger target tissue area than the V or J shapes.

Likewise, the shapes may be formed by differing arrangements of individual leads or portions of leads. For example, the above described "V" shape may be formed by a longer flex circuit lead which is creased and a smaller flex circuit bonded at the crease to form the construct with an interconnect at the crease.

Figure 21A:
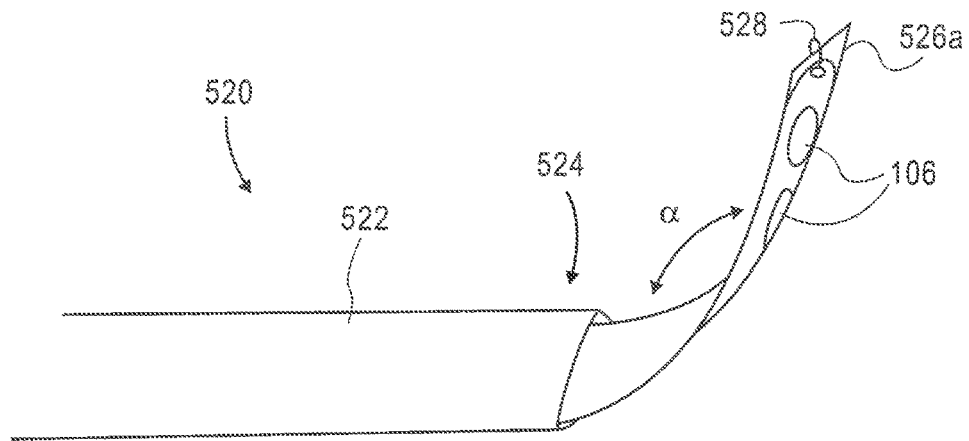
FIG. 21A-21B illustrate a delivery device comprises a flattened tube having a distal end and a pair of obturators which are advanceable out of the distal end.
Figure 21B:
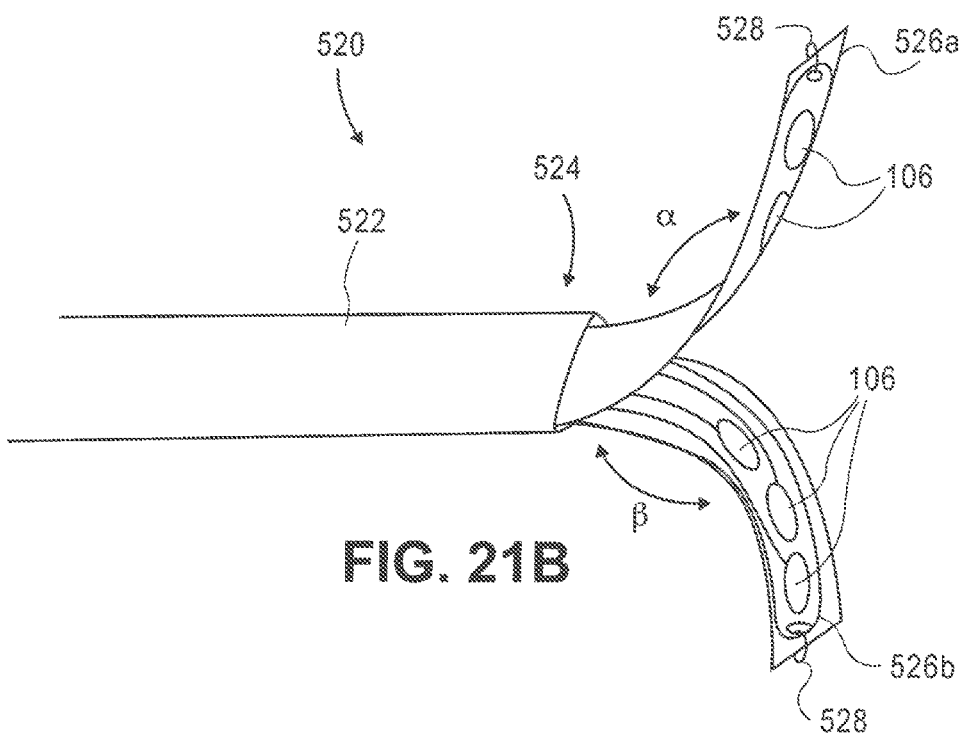

Delivery of the above described shaped lead 500 can be accomplished by a variety of methods. For example, the lead 500 may be delivered with the use of a delivery device such as illustrated in FIGS. 21A-21B. In this embodiment, the delivery device 520 comprises a flattened tube 522 having a distal end 524 and a pair of obturators 526*a*, 526*b* which are advanceable out of the distal end 524. The obturators 526*a*, 526*b* are each comprised of a preformed spring metal or memory metal which is able to curve or bend to form an angle (such as angle .alpha. or angle .beta.) in relation to the flattened tube 522.

FIG. 21A illustrates a first obturator 526a extending from the distal end 524 of the tube 522. One of the individual flex circuit leads 100a is attached to the obturator 526a, such as with the use of a hook 528 which holds the lead 100a in place near the distal tip of the obturator 526a during deployment. The obturator 526a bluntly dissects tissue as it is advanced, drawing the lead 100a into the dissected tissue. FIG. 21B illustrates a second obturator 526b extending from the distal end 524 of the tube 522. Another individual flex circuit lead 100b is attached to the obturator 526b, such as with the use of a hook 528. This obturator 526b bluntly dissects tissue on the opposite side of the target so that the target lies near or within the "V" of the obturators 526a,526b (and therefore between the electrodes 106 of the leads 100a, 100b).

Once deployed, the leads 100a, 100b are released from the hooks 528 and the obturators 526a, 526b are retracted into the tube 522, leaving the leads 100a, 100b behind implanted in a "V" shaped configuration. Appropriate electrode pairs may then be selected for stimulation of the tissue area therebetween based on patient interview for best relief of pain (in the case of DRG stimulation).

Figure 22:
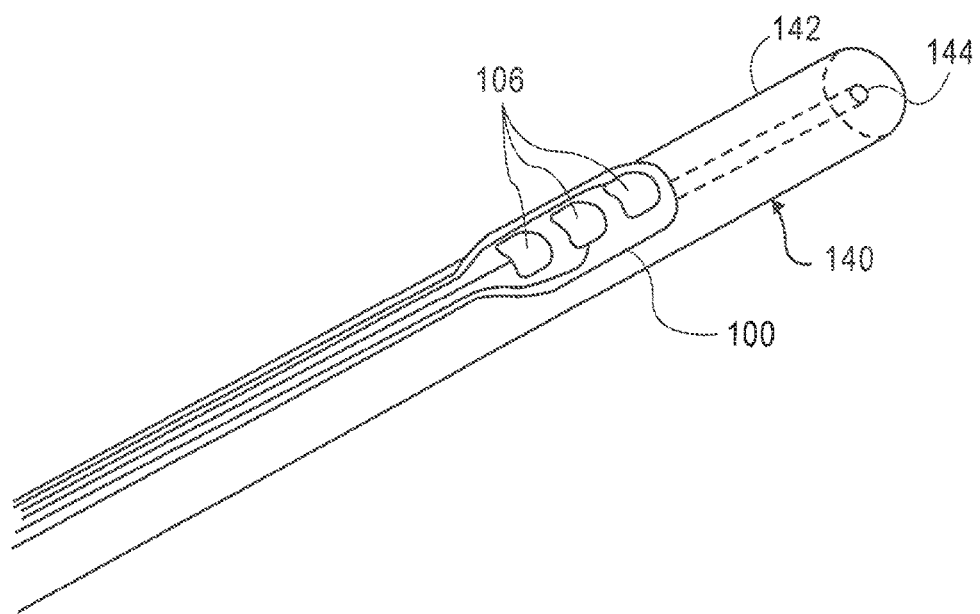
FIG. 22 illustrates a flexible circuit lead attached to a delivery device.
Figure 23:
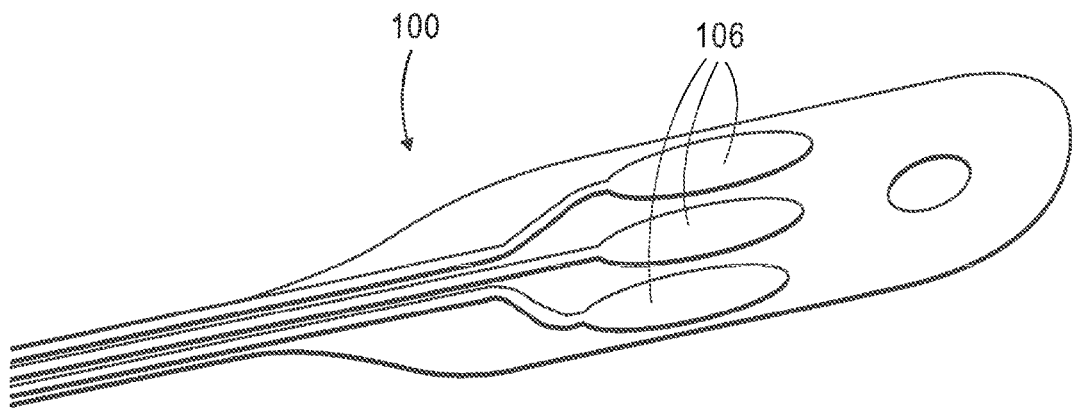
FIG. 23 illustrates a flexible circuit lead particularly suited for wrapping around a catheter.

The flexible circuit leads 100 of the present invention are particularly suitable for implantation in areas of the human body which benefit from highly thin and flexible leads. However, in some portions of the anatomy, delivery of such thin and flexible leads may be challenging due to tortuous or constrained delivery paths. Therefore, the flexible circuit leads 100 may be attached to a delivery device, such as a delivery catheter 140, as illustrated in FIG. 22. The delivery catheter 140 comprises an elongate shaft 142 having a lumen 144 therethrough for passage of a stylet. Thus, the catheter 140 may be comprised of a flexible polymer material to retain the desirable flexibility of the lead 100 yet provide sufficient rigidity for deliverability. In some embodiments, the delivery catheter 140 remains in place with the flexible circuit lead thereattached wherein both remain implanted. In such embodiments, the flexible circuit lead 100 may wrap around the catheter 140 so as to provide electrodes 106 on various surfaces of the catheter 140. FIG. 23 illustrates a flexible circuit lead 100 particularly suited for wrapping around a catheter 140. Here, the electrodes 106 are aligned in a lateral row so that the electrodes 106 will wrap around the circumference of the delivery catheter 140 when mounted thereon. It may be appreciated that any of the flexible leads 100 described herein may be mounted on or attached to a delivery device.

The leads of the present invention are typically passable through a 16 gauge needle, 17 gauge needle, 18 gauge needle or a smaller needle. In some embodiments, the electrode(s) of the present invention have a less than 3 mm square area, preferably less than 2 mm square area. In some embodiments, the electrodes have an approximately 0.6-1 mm square area.

Such reduced dimensions in electrode area and overall size (e.g. outer diameter) are possible due to the increased specificity of the stimulation energy. By positioning at least one of the electrodes on, near or about the desired target tissue, such as the dorsal root ganglion, the stimulation energy is supplied directly to the target anatomy (i.e. the DRG). Thus, a lower power may be used than with a leads which is positioned at a greater distance from the target anatomy. For example, the peak power output of the leads of the present invention are typically in the range of approximately 20 .mu.W-0.5 mW. Such reduction in power requirement for the leads of the present invention may in turn eliminate the need to recharge the power source in the implanted pulse generator (IPG). Moreover, the proximity to the stimulation site also reduce the total amount of energy required to produce an action potential, thus decreasing the time-averaged power significantly and extending battery life.

Figure 24:
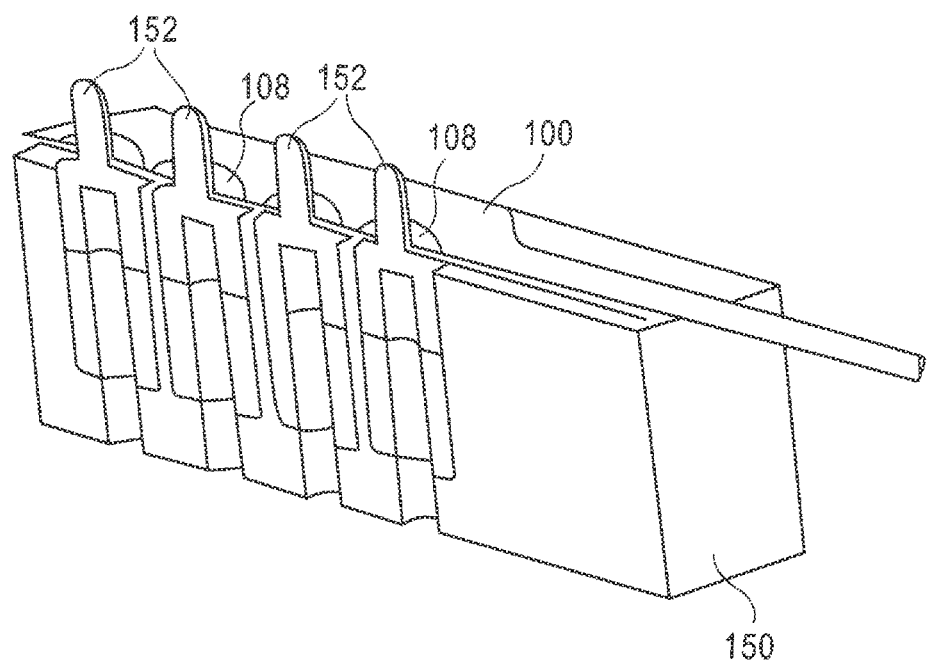
FIGS. 24-25 illustrate an example connector of the present invention.
Figure 25:
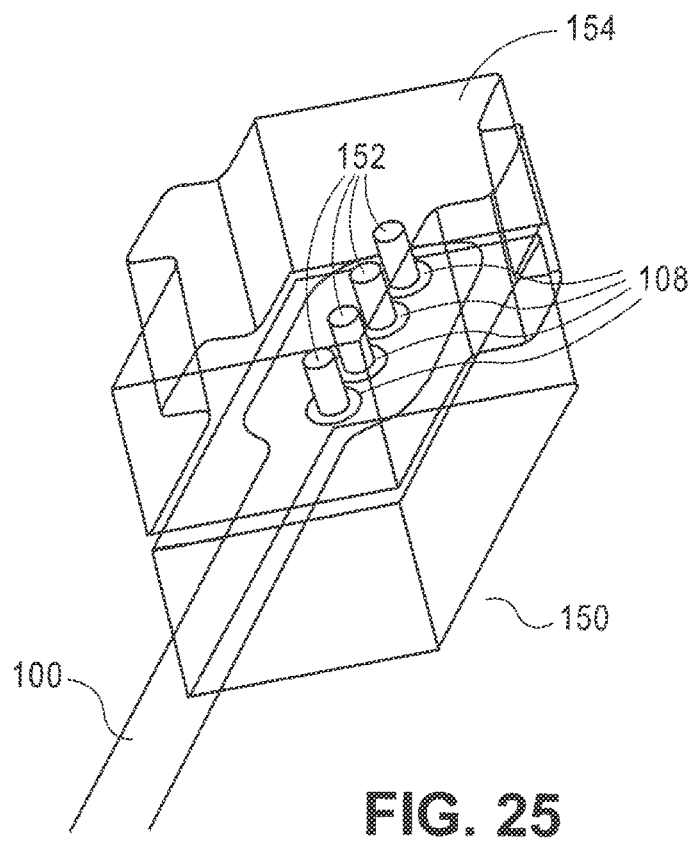

As described previously, the proximal end 104 of each lead 100 is joinable with an IPG to supply stimulation energy to the electrodes 106. FIGS. 24-25 illustrate an example proximal end 104 joined with a connector 150 or portion of an IPG. As shown, the proximal end 104 includes one or more contact pads 108 which are electrically connectable to the connector 150 via one or more pins 152. As shown in cross-section in FIG. 24, the connector 150 is able to make multiple connections with the flexible circuit lead 100. The contact pads 108 are placed over pins 152 that serve as both a means of locating the flexible circuit lead 100 and making the connection with the conductive material of the contact pads 108. Once the proximal end 104 of the lead 100 is placed over the pins 152 a cover 154 is snapped into place, as shown in FIG. 25. The act of snapping the cover 154 on the pins 152 makes the electrical connection between the contact pads 108 and the IPG and can connect many contact pads 108 with just one connection action.

The connector cover 154 snaps in place with a predictable and significant force, enough to maintain the connection. The pins 152 are spring loaded to maintain the correct connection force. The springs may be comprised of a flexible polymer, such as polyurethane or silicone, or a metal. The springs may be separate or built into the pins 152 that make the connection via MEMS or Wire EDM.

It may be appreciated that this connector 150 may be used for any multiple lead connection that benefits from a simplified means for connection. Such application may be for use with a medical device or any electronics connections.

Although the foregoing Invention has been described in some detail by way of illustration and example, for purposes of clarity of understanding, it will be obvious that various alternatives, modifications and equivalents may be used and the above description should not be taken as limiting in scope of the invention.

The invention claimed is:

1. A system for stimulating the dorsal root ganglion of a patient, comprising:
a first elongate flexible implantable dielectric structure comprising a first proximal end adapted to receive first stimulation pulses from an implantable pulse generator, a first distal end adapted to apply the first stimulation pulses to the dorsal root ganglion of the patient, and a first medial portion connecting the first proximal end and the first distal end, wherein the first distal end comprises a first electrode; and
a second elongate flexible implantable dielectric structure comprising a second proximal end adapted to receive second stimulation pulses from the implantable pulse generator, a first distal end adapted to apply the second stimulation pulses to the dorsal root ganglion of the patient, and a second medial portion connecting the second proximal end and the second distal end, wherein the second distal end comprises a second electrode;
wherein the first and second proximal ends and first and second medial portions are bonded together along a central longitudinal axis so that the first and second elongate flexible implantable dielectric structures are configured to extend lengthwise along the central longitudinal axis, wherein the first and second electrodes are disposed on first and second inner surfaces of the first and second distal ends respectively and are configured to be implanted at least partially within a vertebral foramen containing the dorsal root ganglion to direct stimulation energy toward the central longitudinal axis;

wherein at least one of the first and second distal ends is configured to move away from the central longitudinal axis while the first and second proximal ends are joined to allow the dorsal root ganglion to be positioned at least partially between the first and second distal ends to receive the stimulation energy that is directed by the first and second electrodes toward the central longitudinal axis.

2. A system as in claim 1, wherein the first distal end is movable by recoil force.

3. A system as in claim 1, wherein the first distal end is attachable to a first obturator which is capable of moving the first distal end.

4. A system as in claim 3, wherein the first obturator is configured to dissect tissue while it moves the first distal end.

5. A system as in claim 3, wherein the first obturator is advanceable from a delivery device so as to advance the first distal end and move the first distal end away from the second distal end.

6. A system as in claim 1, wherein the first elongate structure and the second elongate structure comprise a dielectric film.

7. A system as in claim 6, wherein the first dielectric film and the second dielectric film has a thickness in the range of approximately 7.5 to 125 µm.

8. A system as in claim 6, wherein the first dielectric film and the second dielectric film has a thickness in the range of approximately 0.5-2 mils.

9. A system as in claim 1, further comprising: a first contact pad and a first conductive trace extending from the first contact pad to the first electrode, a second contact pad and a second conductive trace extending from the second contact pad to the second electrode, wherein the first contact pad and the second contact pad provide electrical connection from the first electrode and the second electrode to the implantable pulse generator.

10. A system as in claim 1, wherein the first and second distal ends are passable through a needle.

11. A system as in claim 1, wherein the first distal end of the first elongate structure includes at least one fold, wherein the first distal end is configured to pass through a delivery device while in an unfolded position and wherein the first distal end deploys upon release from the delivery device toward a folded position.

12. A system as in claim 11, wherein the second distal end includes at least one fold, wherein the second distal end is configured to pass through the delivery device while in an unfolded position and wherein the second distal end deploys upon release from the delivery device toward a folded position so that the first and second distal ends deploy by moving away from each other so as to at least partially surround the dorsal root ganglion.

13. A system as in claim 12, wherein the first and second distal ends move independently.

14. A system as in claim 12, wherein the deployed first and second distal ends together form a V-shape.

15. A system as in claim 11, wherein the first and second distal ends are configured to be passable through a needle prior to deployment.

16. A system as in claim 11, wherein the first inner surface faces away from the at least one fold.

17. A system as in claim 16, wherein the first proximal end has at least one contact pad, wherein the at least one contact pad is disposed on an opposite surface of the first inner surface and faces the at least one fold.

18. A system as in claim 17, wherein the at least one fold is disposed between the first electrode and the at least one contact pad.

19. A system as in claim 1, wherein the at least one of the first and second distal ends are moveable away from the longitudinal axis by bending or curving.

20. A system as in claim 1, wherein the at least one of the first and second distal ends are moveable away from the longitudinal axis by folding.

* * * * *